(12) United States Patent
Naglah et al.

(10) Patent No.: US 9,969,768 B1
(45) Date of Patent: May 15, 2018

(54) OLEANOLIC ACID METHYL ESTER DERIVATIVES

(71) Applicant: KING SAUD UNIVERSITY, Riyadh (SA)

(72) Inventors: Ahmed M. Naglah, Riyadh (SA); Abd El-Galil E. Amr, Riyadh (SA); Mohamed A. Al-Omar, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days. days.

(21) Appl. No.: 15/815,587

(22) Filed: Nov. 16, 2017

(51) Int. Cl.
| | |
|---|---|
| *C07J 63/00* | (2006.01) |
| *C07J 53/00* | (2006.01) |
| *C07D 213/36* | (2006.01) |
| *A61K 31/56* | (2006.01) |
| *C07B 43/04* | (2006.01) |
| *C07B 49/00* | (2006.01) |
| *C07D 265/30* | (2006.01) |

(52) U.S. Cl.
CPC ............. *C07J 63/008* (2013.01); *A61K 31/56* (2013.01); *C07B 43/04* (2013.01); *C07B 49/00* (2013.01); *C07D 213/36* (2013.01); *C07D 265/30* (2013.01); *C07J 53/002* (2013.01)

(58) Field of Classification Search
CPC ................................ A61K 31/21; C07J 63/008
See application file for complete search history.

(56) References Cited

U.S. PATENT DOCUMENTS

| | | | |
|---|---|---|---|
| 5,519,008 | A | 5/1996 | Rao et al. |
| 7,820,656 | B2 | 10/2010 | Kim |
| 7,915,402 | B2 | 3/2011 | Anderson et al. |
| 8,519,127 | B2 | 8/2013 | Bickerdike et al. |
| 9,156,801 | B2 * | 10/2015 | Xu .................... C07J 63/00 |
| 9,556,201 | B2 | 1/2017 | Ng et al. |
| 2005/0019435 | A1 | 1/2005 | Young |
| 2010/0048911 | A1 | 2/2010 | Jiang et al. |
| 2017/0196890 | A1 | 7/2017 | Yu et al. |

FOREIGN PATENT DOCUMENTS

| | | |
|---|---|---|
| WO | 2008/071169 A2 | 6/2008 |
| WO | 2012-020019 A1 | 2/2012 |

OTHER PUBLICATIONS

Pollier, J., Goossens, A. (2012). Oleanolic acid. Phytochemistry. 77(5): 10-15.
Liu J. (1995). Pharmacology of oleanolic acid and ursolic acid. Journal of Ethnopharmacology. 49 (2): 57-68.
Jump Y., Wang, Q., Zhang, Z., Peng, Y., Qiu, Y., Shi, Y-Y., Zheng, Y-X., Xiao, S-L., Wang, H., Huang, X., Zhu, L., Chen, K., Zhao, C., Zhang, C., Yu, M., Sun, D., Zhang, L., Zhou, D. (2013). Development of oleanane-type triterpenes as a new class of HCV entry inhibitors. Journal of Medicinal Chemistry. 56 (11): 4300-4319.
Albena T. D.K., Karen T. L., Katherine K. S., David H., Xiangqun G., Nanjoo S., Charlotte W., Renee R., Tadashi H., Gordon W. G., Michael B. S., Paul T. (2005). Extremely potent triterpenoid inducers of the phase 2 response: Correlations of protection against oxidant and inflammatory stress. Proceedings of the National Academy of Sciences of the United States of America. 102 (12): 4584-4589.
Mariano W. P., Cecilia L., Cristina T., Guillermo S-H. (2013). 1,2,3-Triazole-substituted oleanolic acid derivatives: Synthesis and antiproliferative activity. Molecules. 18: 7661-7674.
Fuhao C., Xin X., Guoliang L., Shun G., Kuo X., Yan G., Bing X., Mina W., Huazheng Z., Yuzhong Z., Penglong W., Haimin L., (2014). Amino acid derivatives of ligustrazine-oleanolic acid as new cytotoxic agents. Molecules. 19: 18215-18231.
Chu T., Linhui Z., Yu C., Rui Q., ZhiNan M., Jing X., Guangzhong Y. (2014). Synthesis and biological evaluation of oleanolic acid derivative-chalcone conjugates as aglucosidase inhibitors. RSC Adv., 4: 10862-10874.
Jose M. C., Angeles G., Teresa D., Mirela R., Jose A. C. (2013). Biochemical basis of the antidiabetic activity of oleanolic acid and related pentacyclic triterpenes. Diabetes. 62(6): 1791-1799.
Xing-hua Z., Jufang Y., LiFan, W., Dacheng Y. (2011). Synthesis and antidiabetic activity of β-acetamido ketones. Acta Pharmaceutics Sinica B. 1(2):100-105.
Chapdelaine P., Tremblay R. R., Dube, J. Y. (1978). P-Nitrophenol-alpha-D-gluco-pyranoside as substrate for measurement of maltase activity in human semen. Clin. Chem., 24: 208-211.
Dunn, J.S., Letchie, N. G. (1943). Experimental alloxan diabetes in the rat. The Lancet, 242(6265): 384-387.

* cited by examiner

*Primary Examiner* — Paul A Zucker
(74) *Attorney, Agent, or Firm* — Richard C. Litman

(57) ABSTRACT

Oleanolic acid methyl ester derivatives demonstrate potent anti-diabetic activities. In in vitro anti-diabetic testing, the derivatives showed more potency regarding dipeptidyl peptidase-4 (DPP-IV) inhibitor activity, peroxisome proliferator-activated receptors (PPARs) agonist activity, and α-Glucosidase inhibitors activity, as compared to reference standards oleanolic acid and acarbose. In in vivo oral hypoglycemic testing, both acute and sub-acute studies demonstrated that the derivatives had high potency and long duration of action compared to the reference standards pioglitazone, acarbose and oleanolic acid.

13 Claims, 7 Drawing Sheets

OLEANOLIC ACID METHYL ESTER DERIVATIVES

BACKGROUND

1. Field

The disclosure of the present patent application relates generally to certain oleanolic acid derivatives useful as anti-diabetic compounds, and particularly to oleanolic acid methyl ester derivatives confined to ring A that demonstrate particularly potent anti-diabetic activity.

2. Description of the Related Art

Oleanolic acid is a naturally occurring pentacyclic triterpenoid related to betulinic acid. It is widely available in food and plants where it exists as a free acid or as an aglycone of triterpenoid saponins. "Oleanolic Acid," Pollier, J., Goossens, A., *Phytochemistry* 77(5): 10-15 (2012). Oleanolic acid provides hepatoprotective, antitumor, and antiviral properties. "Pharmacology of oleanolic acid and ursolic acid," Liu J., *Journal of Ethno-pharmacology* 49(2): 57-68 (1995). Also, oleanolic acid has anti-human immunodeficiency virus (anti-HIV) and anti-hepatitis C virus (anti-HCV) activities in vitro. "Development of oleanane-type triterpenes as a new class of HCV entry inhibitors," Jump Y., Wang, Q., Zhang, Z., Peng, Y., Qiu, Y., Shi, Y-Y., Zheng, Y-X., Xiao, S-L., Wang, H., Huang, X., Zhu, L., Chen, K., Zhao, C., Zhang, C., Yu, M., Sun, D., Zhang, L., Zhou, D., *Journal of Medicinal Chemistry* 56 (11): 4300-4319 (2013).

Several chemical derivatives of oleanolic acid have previously been synthesized. These derivatives demonstrated potent anti-inflammatory activities. The mechanisms of action were thought to be either induction by Interferon gamma (IFN-γ) of inducible nitric oxide synthase (iNOS), and/or inhibition of cyclooxygenase 2 (Cox-2). "Extremely potent triterpenoid inducers of the phase 2 response: Correlations of protection against oxidant and inflammatory stress," Albena T. D. 0K., Karen T. L., Katherine K. S., David H., Xiangqun G., Nanjoo S., Charlotte W., Renee R., Tadashi H., Gordon W. G., Michael B. S., Paul T., *Proceedings of the National Academy of Sciences of the United States of America* 102(12): 4584-4589 (2005).

Further, 1,2,3-Triazole-Substituted Oleanolic Acid Derivatives were synthesized and showed potent Antiproliferative activities. "1,2,3-Triazole-substituted oleanolic acid derivatives: Synthesis and antiproliferative activity," Mariano W. P., Cecilia L., Cristina T., Guillermo S-H., *Molecules* 18:7661-74 (2013).

A series of novel ligustrazine-oleanolic acid (TOA) derivatives were designed, and synthesized by conjugating amino acids to the 3-hydroxy group of TOA by ester bonds and were found to have potent cytotoxic activities. "Amino acid derivatives of ligustrazine-oleanolic acid as new cytotoxic agents," Fuhao C., Xin X., Guoliang L., Shun G., Kuo X., Yan G., Bing X., Mina W., Huazheng Z., Yuzhong Z., Penglong W., Haimin L., *Molecules* 19:18215-31 (2014).

A series of oleanolic acid derivative-chalcone conjugates were found to have α-glucosidase inhibitor activities. "Synthesis and biologic evaluation of oleanolic acid derivative-chalcone conjugates as aglucosidase inhibitors," Chu T., Linhui Z., Yu C., Rui Q., ZhiNan M., Jing X., Guangzhong Y., *RSC Adv.* 4:10862-74 (2014). Oleanolic acid derivatives having potent anti-diabetic activities have also been studied. Jose M. C., Angeles G., Teresa D., Mirela R., Jose A. C., "Biochemical basis of the anti-diabetic activity of oleanolic acid and related pentacyclic triterpenes," *Diabetes* 62(6): 1791-1799 (2013).

Thus, it would be desirable to synthesize and identify oleanolic acid methyl ester derivatives for anti-diabetic activity.

SUMMARY

An oleanolic acid methyl ester derivative can include methyl-2-{4-pyridylidene}-3-oxo-18β-Olean-12-en-28-oate (Compound 2), having the structural formula

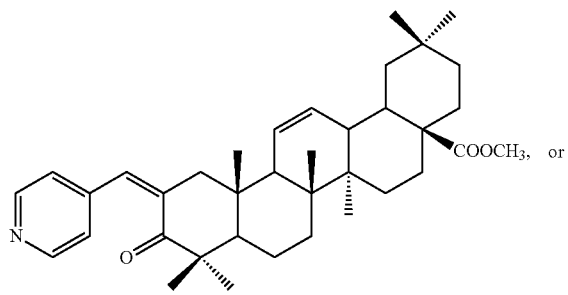

methyl-2-{phenyl-(4-pyridyl)-methane}-3-oxo-18β-olean-12-en-28-oate (Compound 3), having the structural formula

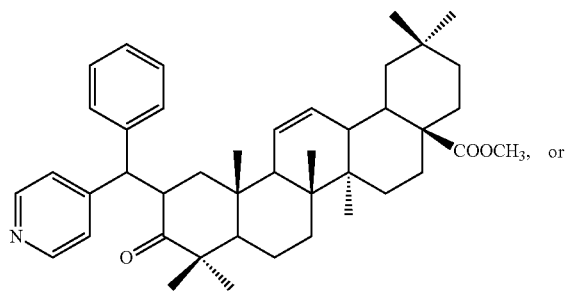

methyl-2-{(4-pyridyl)-N-morpholinylmethane}-3-oxo-18β-olean-12-en-28-oate (Compound 4), having the structural formula

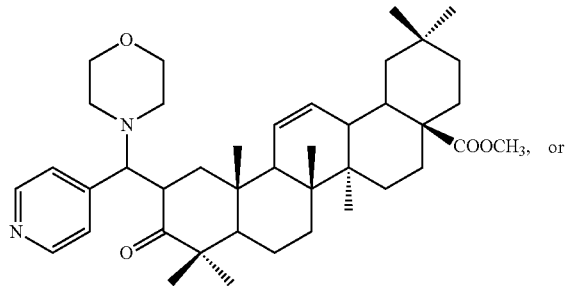

methyl-2-{N-(morpholino)methane}-3-oxo-18β-olean-12-ene-28-oate (Compound 5), having the structural formula

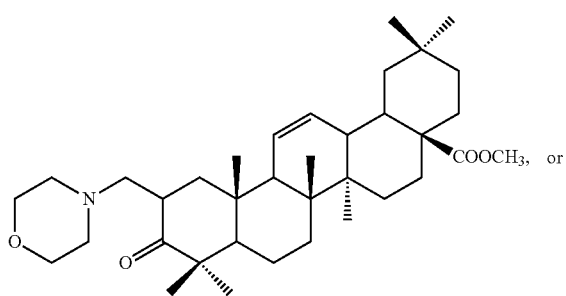

methyl-2-{N-(morpholino) methane}-3β-hydroxy-3α-phenyl-18β-Olean-12-ene-28-oate (Compound 6), having the structural formula

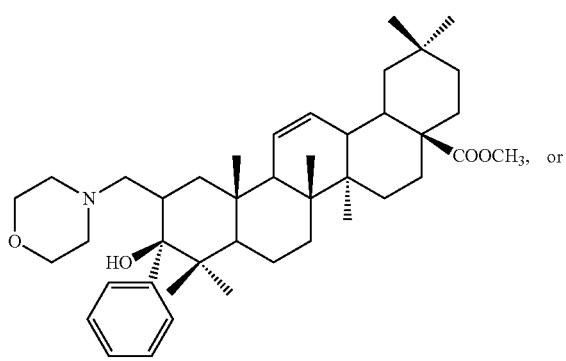

a pharmaceutically acceptable salt of Compound 2, Compound 3, Compound 4, Compound 5, or compound 6.

The oleanolic acid methyl ester derivatives exhibit in vitro anti-diabetic activities in vivo oral hypoglycemic activities.

These and other features of the present disclosure will become readily apparent upon further review of the following specification and drawings.

BRIEF DESCRIPTION OF THE DRAWINGS

Similar reference characters denote corresponding features through the drawings.

DETAILED DESCRIPTION OF THE PREFERRED EMBODIMENTS

An oleanolic acid methyl ester derivative can include methyl-2-{4-pyridylidene}-3-oxo-18β-Olean-12-en-28-oate (Compound 2), having the structural formula

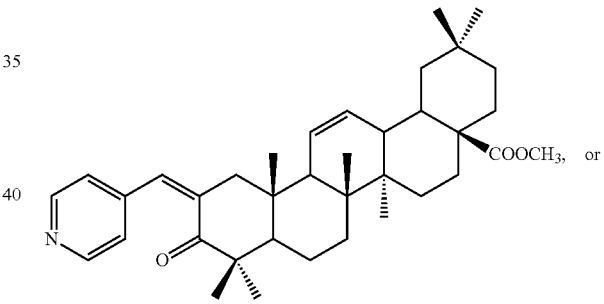

methyl-2-{phenyl-(4-pyridyl)-methane}-3-oxo-18β-olean-12-en-28-oate (Compound 3), having the structural formula

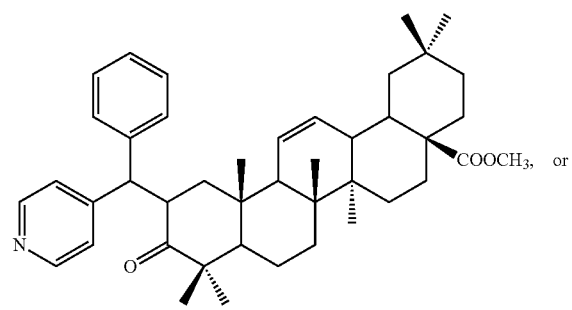

methyl-2-{(4-pyridyl)-N-morpholinylmethane}-3-oxo-18β-olean-12-en-28-oate (Compound 4), having the structural formula

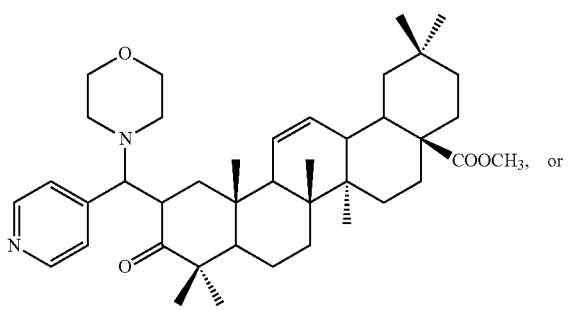

methyl-2-{N-(morpholino)methane}-3-oxo-18β-olean-12-ene-28-oate (Compound 5), having the structural formula

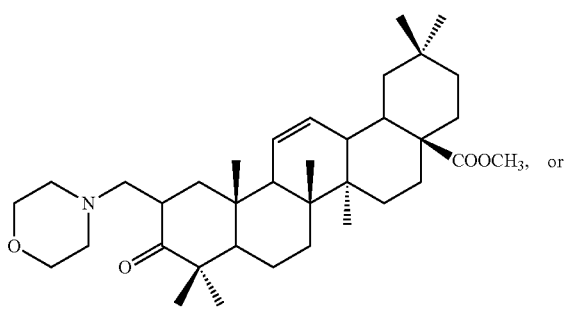

methyl-2-{N-(morpholino) methane}-3β-hydroxy-3α-phenyl-18β-Olean-12-ene-28-oate (Compound 6), having the structural formula

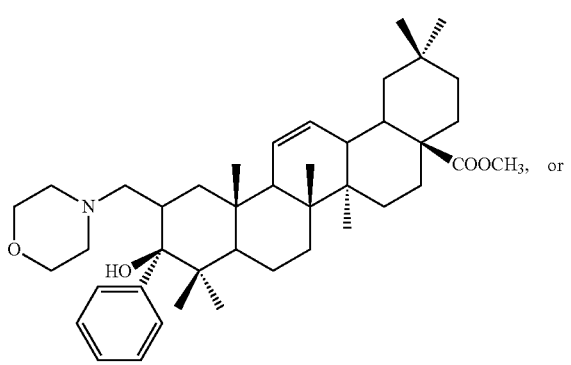

a pharmaceutically acceptable salt of Compound 2, Compound 3, Compound 4, Compound 5, or compound 6.

The oleanolic acid methyl ester derivatives can be used as an active ingredient of pharmaceuticals for the treatment or prevention of metabolic syndrome and/or diabetes. The diabetes can include diabetes mellitus type 2. The oleanolic acid methyl ester derivatives can be included as an ingredient in functional foods. A method of making the oleanolic acid methyl ester derivatives is exemplified herein.

Figure 1:
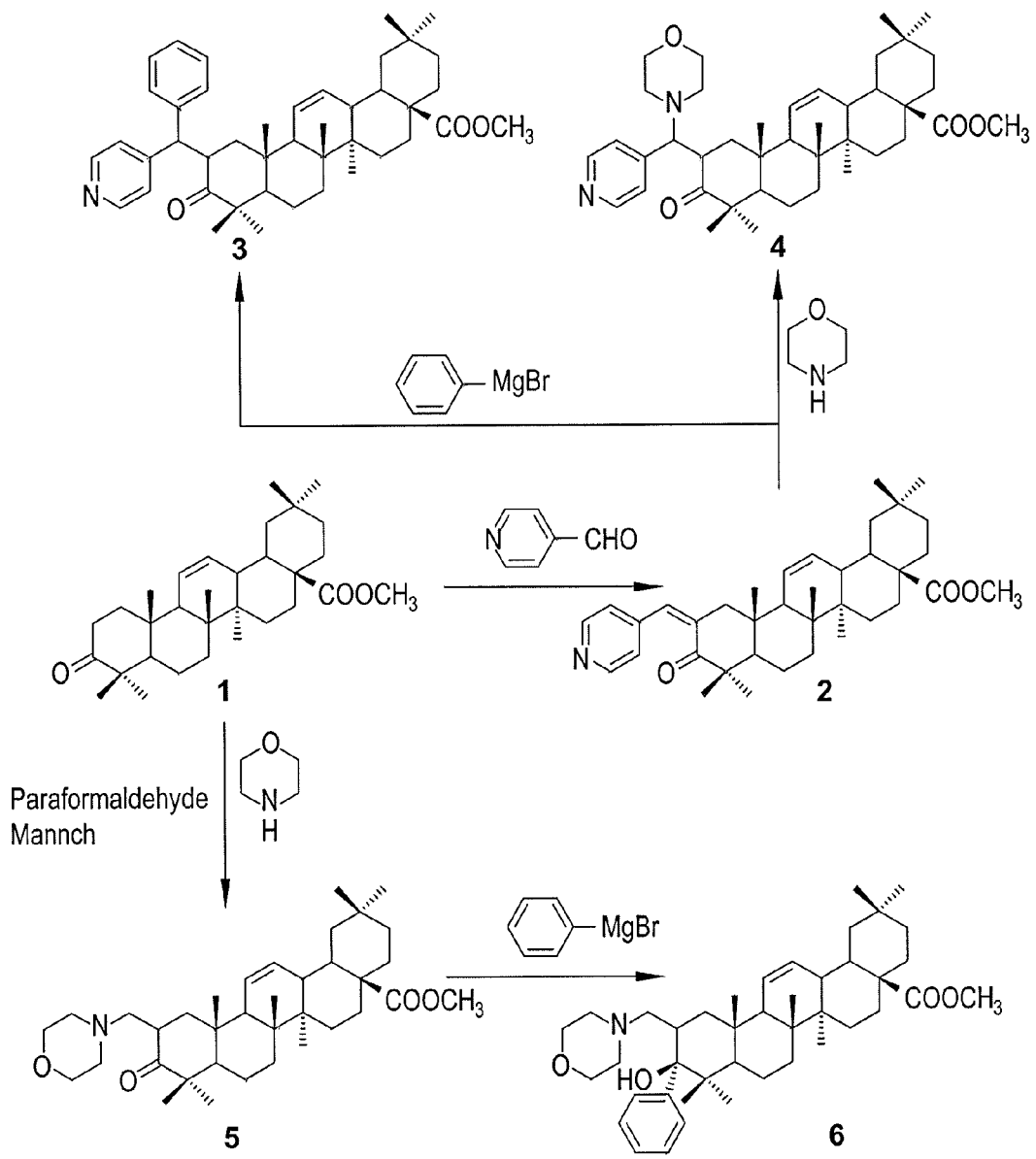
FIG. 1 is a reaction scheme for preparing Compounds 2-6.

FIG. 1 depicts a reaction scheme by which Compounds 2-6 can be prepared. For synthesis of Compound 2, Compound 1 (3-oxo-oleanolic acid methyl ester) can be treated with 4-pyridinecarboxaldehyde and subjected to Aldol condensation to provide the corresponding arylidiene derivative, Compound 2. To prepare Compound 3 (the 1, 4 Grignard addition product), the arylidiene derivative (Compound 2) can be treated with phenyl magnesium bromide under Grignard reaction conditions. To prepare Compound 4 (the 1, 4 Michael addition product), the arylidiene derivative (Compound 2) can be treated with morpholine.

For synthesis of Compound 5, the 3-oxo-oleanolic acid methyl ester (Compound 1) can be treated with morpholine and paraformaldehyde, resulting in a Mannich reaction. For synthesis of Compound 6 (the 1, 2 Grignard addition product), Compound 5 can be treated with phenyl magnesium bromide, resulting in a Grignard reaction.

The oleanolic acid methyl ester derivatives can be used to treat diabetes and/or metabolic syndrome. As described in detail in the Examples below, the oleanolic acid methyl ester derivatives exhibited potent anti-diabetic activities. For example, the oleanolic acid methyl ester derivatives exhibited in vivo oral hypoglycemic activity when tested on mice. The oleanolic acid methyl ester derivatives exhibited more than double the activity of pioglitazone and acarbose after two hours of administration.

Through complex and multi-factorial mechanisms, oleanolic acid provides beneficial effects against diabetes and metabolic syndrome. Metabolic syndrome is a cluster of conditions—increased blood pressure, high blood sugar, excess body fat especially around the waist, and abnormal cholesterol or triglyceride levels. These conditions together increase the risk of heart disease and other health problems in an individual, including stroke and diabetes.

Oleanolic acid improves insulin response, preserves functionality and survival of β-cells, and helps protect against complications from diabetes. Oleanolic acid may directly modulate enzymes associated with insulin biosynthesis, secretion, and signaling. However, its major contributions appear to relate to interaction with important transduction pathways.

Many of the effects of oleanolic acid have been associated with activation of the transcription factor, the nuclear factor erythroid 2-related factor 2 (Nrf2). Oleanolic acid appears to induce the expression of antioxidant enzymes and phase II response genes, while blocking nuclear factor kappa-light-chain-enhancer of activated B cells (NF-κB), and repressing the polyol pathway, advanced glycation end products (AGEs) production, and hyperlipidemia. Management of type 2 diabetes requires an integrated approach, including early intervention to prevent or delay the disease progression, and the use of drug therapies to control glycemia and lipidemia in its late stages. Accordingly, the availability of foods or drugs containing effective oleanolic acid derivatives is very desirable and useful.

A pharmaceutically acceptable salt includes any non-toxic salt of the present compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The oleanolic acid methyl ester derivatives can be administered to a patient in need thereof. For example the oleanolic acid methyl ester derivatives can be used to treat or prevent metabolic syndrome, diabetes, or abnormally high blood glucose levels. The oleanolic acid methyl ester derivatives can be administered by any conventional route of administration, including, but not limited to, intravenous, oral, subcutaneous, intramuscular, intradermal and parenteral. Depending on the route of administration, the oleanolic acid methyl ester derivatives can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an oleanolic acid methyl ester derivative. To prepare the pharmaceutical composition, one or more oleanolic acid methyl ester derivatives or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

A pharmaceutical composition including an effective amount of the oleanolic acid methyl ester derivative can be administered to a patient in need thereof. A therapeutically effective amount of the oleanolic acid methyl ester derivative or an amount effective to treat metabolic syndrome or diabetes may be determined initially from in vivo assays described herein and adjusted for specific desired oleanolic acid methyl ester derivatives using routine methods.

The following examples illustrate the present teachings.

Example 1

In Vitro Anti-Diabetic Activities of Compounds 2 to 6

The activities of Compounds 2-6 were evaluated in vitro for DPP-IV Inhibitor activity; PPAR Agonist activity; and α-Glucosidase Inhibitor activity.

DPP-IV Inhibition Activity

A 200 mL reaction system containing DPP-IV (Sigma), a test compound, and 25 mmol/L 4-(2-hydroxyethyl)-1-piperazineethanesulfonic acid (HEPES) buffer (containing 140 mmol/L NaCl, 1% Bovine serum albumin (BSA) and 80 mmol/L $MgCl_2$) was pre-incubated at room temperature for 10 minutes. The reaction was initiated by the addition of DPP-IV, and the reaction mixture was then incubated at room temperature for 25-45 minutes. The fluorescence intensity (F) at excitation 355 nm and emission 460 nm was then measured. A negative control (no test compound) and a blank control (no enzyme) were run simultaneously. The test compounds were initially assayed in duplicate at a concentration of 10 mg/mL. The % inhibition was calculated as $[1-(F_{test\ compound}-F_{blank})/(F_{negative}-F_{blank})]\times 100\%$. If an inhibition of more than 50% was observed, the compound was subsequently tested at six concentrations in duplicate and the $IC_{50}$ value calculated using the XLfit software. Xing-hua Z., Jufang Y., LiFan, W., Dacheng Y., "Synthesis and antidiabetic activity of β-acetamido ketones," Acta Pharmaceutica Sinica 1(2):100-105 (2011).

With regard to the in vitro DPP-IV inhibition activity, the synthesized compounds (Compounds 2-6) exhibited half maximal inhibitory concentration ($IC_{50}$) values ranging from 0.0044 μM to 0.091 μM—much higher potencies than the comparative reference standards used—oleanolic acid (1.21 μM) and acarbose (175.84 μM). The activity of Compounds 1-6 ranked as follows, from highest to lowest potency, when compared by molar concentration: Compound 4 had the highest potency, followed by Compound 3, then Compound 2, then Compound 6, followed by Compound 5, and finally Compound 1. These results are reflected in Table 1.

TABLE 1

| DPP-IV Inhibitor Activity of Compounds 1-6. | |
|---|---|
| Compound | DPP-IV $IC_{50}$ (μM) |
| 1 | 0.091 ± 0.0009 |
| 2 | 0.033 ± 0.0006 |
| 3 | 0.022 ± 0.0004 |
| 4 | 0.0044 ± 0.0005 |
| 5 | 0.062 ± 0.0008 |
| 6 | 0.040 ± 0.0007 |
| Oleanolic acid | 1.21 ± 0.079 |
| Acarbose | 175.84 ± 10.1 |

Values are standard error of mean (±S.E.M.); n = 6 in each group. Statistical analysis by one way analysis of variance (ANOVA) followed by Dunnet test using Graphpad Instat software (P < 0.05).

Figure 2:
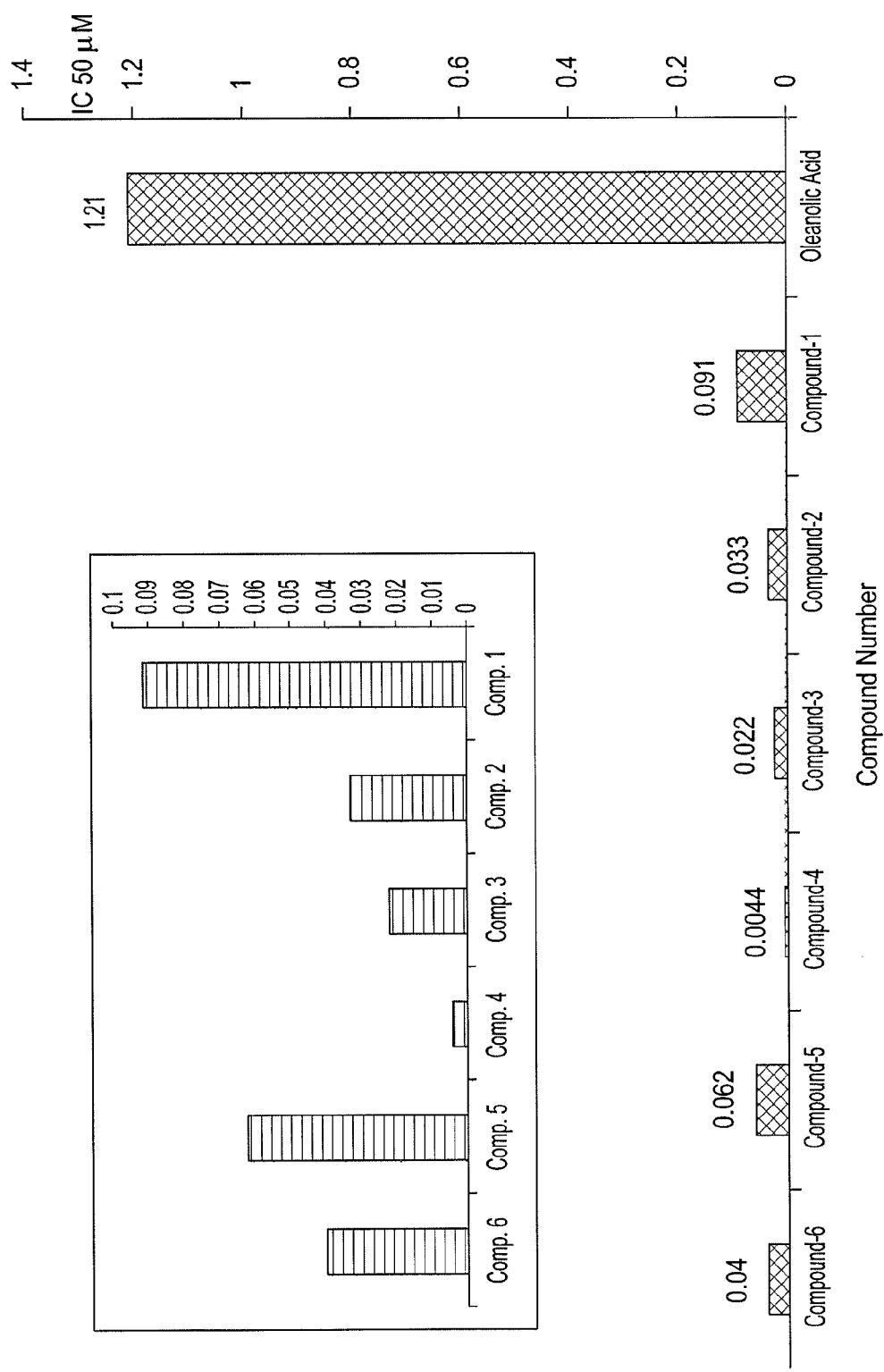
FIG. 2 is a graph showing relative DPP-IV inhibitor activity ($IC_{50}$ concentrations) for Compounds 1-6, compared to oleanolic acid.

These results for Compounds 1-6 and oleanolic acid are also reflected in FIG. 2.

PPAR Agonist Activity

HepG2 cells were cultured in low glucose Dulbecco's Modified Eagle's medium (DMEM) supplemented with 100 U/mL streptomycin and penicillin. One day prior to transfection, the cells were plated in 96-well plates at $1.5\times 10^4$ cells per well. After reaching 70% confluence, plasmid peroxisome proliferator responsive element-luciferase (PPRE-Luc) with firefly luciferase reporter gene and the control plasmid phRL-TK with renilla luciferase reporter gene were transfected into the cells. After 24 hours, the medium was replaced with either fresh medium (negative control) or fresh medium containing a test compound (10 mg/mL) or pioglitazone (positive control). Non-transfected cells were used as blank. After a further 24 hours, the expression of luciferases was measured using the Dual Luciferase Reporter Gene Assay Kit (Promega). The percent activation (T %) was calculated as $[(L1_{sample}-L1_{Blank})/(L1_{Negative}-L1_{Blank})]/[(L2_{Sample}-L2_{Blank})/(L2_{Negative}-L2_{Blank})]\times 100\%$, where L1 represents the value for the value for firefly luciferase and L2 the value for Renilla luciferase. Xing-hua Z., Jufang Y., LiFan, W., Dacheng Y., "Synthesis and antidiabetic activity of β-acetamido ketones," Acta Pharmaceutica Sinica 1(2):100-105 (2011).

With regard to PPAR Agonist activity, Compounds 2-6 exhibited $IC_{50}$ values ranging from 0.0078 μM to 0.12 μM—again demonstrating much more potency than the reference oleanolic acid (at 14.9 μM). The activity of Compounds 1-6 ranked as follows, from highest to lowest potency, when compared by molar concentration: Compound 4 had the highest potency, followed by Compound 3, then Compound 2, then Compound 6, followed by Compound 5, and final Compound 1. These results are summarized in Table 2.

TABLE 2

PPAR Agonist Inhibitor Activity of Compounds 1-6.

| Compound | PPAR $IC_{50}$ (μM) |
|---|---|
| 1 | 0.12 ± 0.004 |
| 2 | 0.057 ± 0.006 |
| 3 | 0.034 ± 0.004 |
| 4 | 0.0078 ± 0.0005 |
| 5 | 0.081 ± 0.005 |
| 6 | 0.061 ± 0.007 |
| Oleanolic acid | 14.9 ± 0.9 |

Values are mean ± S.E.M, n = 6 in each group. Statistical analysis by one way ANOVA followed by Dunnet test using Graphpad Instat software. (P < 0.05).

Figure 3:
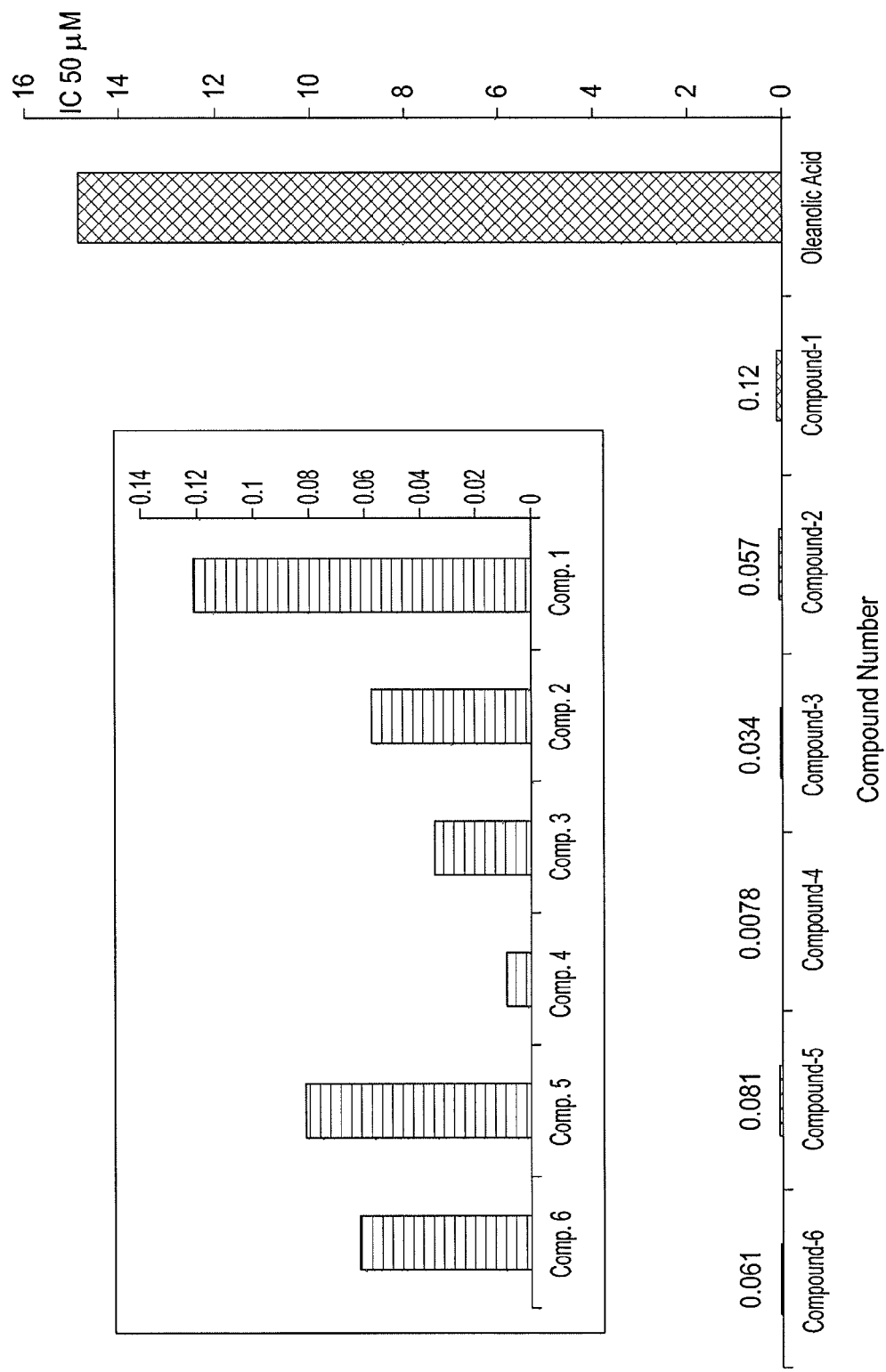
FIG. 3 is a graph showing relative PPAR Agonist activity ($IC_{50}$ concentrations) for Compounds 1-6, compared to oleanolic acid.

These results for Compounds 1-6 and oleanolic acid are also reflected in FIG. 3.

Anti-Diabetic Bioassay α-Glucosidase Inhibitory Activity Determination

The α-Glucosidase inhibitory activity of each compound was determined according to the chromogenic method described by Chapdelaine et al with slight modifications. See, Chapdelaine P., Tremblay R. R., Dube, J. Y., "P-Nitrophenol-alpha-D-gluco-pyranoside as substrate for measurement of maltase activity in human semen," *Clin. Chem.*, 24: 208-211 (1978). α-Glucosidase from *Saccharomyces cerevisiae* and substrate solution P-Nitrophenyl-β-D-glucuronide (PNPG) were prepared with 0.1 mol $L^{-1}$ of Na-phosphate buffer (pH 6.8). The inhibitors were reconstituted in 80 mL phosphate buffer in a 96-well microplate and incubated with 30 mL α-Glucosidase at 37° C. for 15 minutes, and then 30 μL substrate was added. After incubation with substrate for 5 minutes, release of p-nitrophenol was measured at 405 nm by spectrophotometry. Percentage of enzyme inhibition was calculated according to {1−($A_{sample}$−$A_{blank}$)/$A_{control}$}×100, where $A_{sample}$ represents absorbance of test samples, $A_{control}$ represents absorbance of solution without sample, and A blank represents absorbance in presence of solution without substrate.

With regard to α-Glucosidase Inhibitor activity, Compounds 2-6 exhibited $IC_{50}$ values ranging from 0.087 μM to 1.70 μM—again much more potent results than for the reference standards, oleanolic acid (102.3 μM) and acarbose (131.2 μM). The activity of the tested compounds again exhibited the following descending potency order: Compound 4 had the highest potency, followed by Compound 3, then Compound 2, then Compound 6, followed by Compound 5, and finally Compound 1. The results are summarized in Table 3.

TABLE 3

α-Glucosidase Inhibitor Activity of Compounds 1-6

| Compound | α-Glucosidase $IC_{50}$ (μM) |
|---|---|
| 1 | 1.70 ± 0.03 |
| 2 | 0.245 ± 0.004 |
| 3 | 0.123 ± 0.004 |
| 4 | 0.087 ± 0.001 |
| 5 | 0.690 ± 0.006 |
| 6 | 0.451 ± 0.005 |

TABLE 3-continued

α-Glucosidase Inhibitor Activity of Compounds 1-6

| Compound | α-Glucosidase $IC_{50}$ (μM) |
|---|---|
| Oleanolic acid | 102.3 ± 2.37 |
| Acarbose | 131.2 ± 1.13 |

Values are mean ± S.E.M, n = 6 in each group. Statistical analysis by one way ANOVA followed by Dunnet test using Graphpad Instat software. (P < 0.05).

Figure 4:
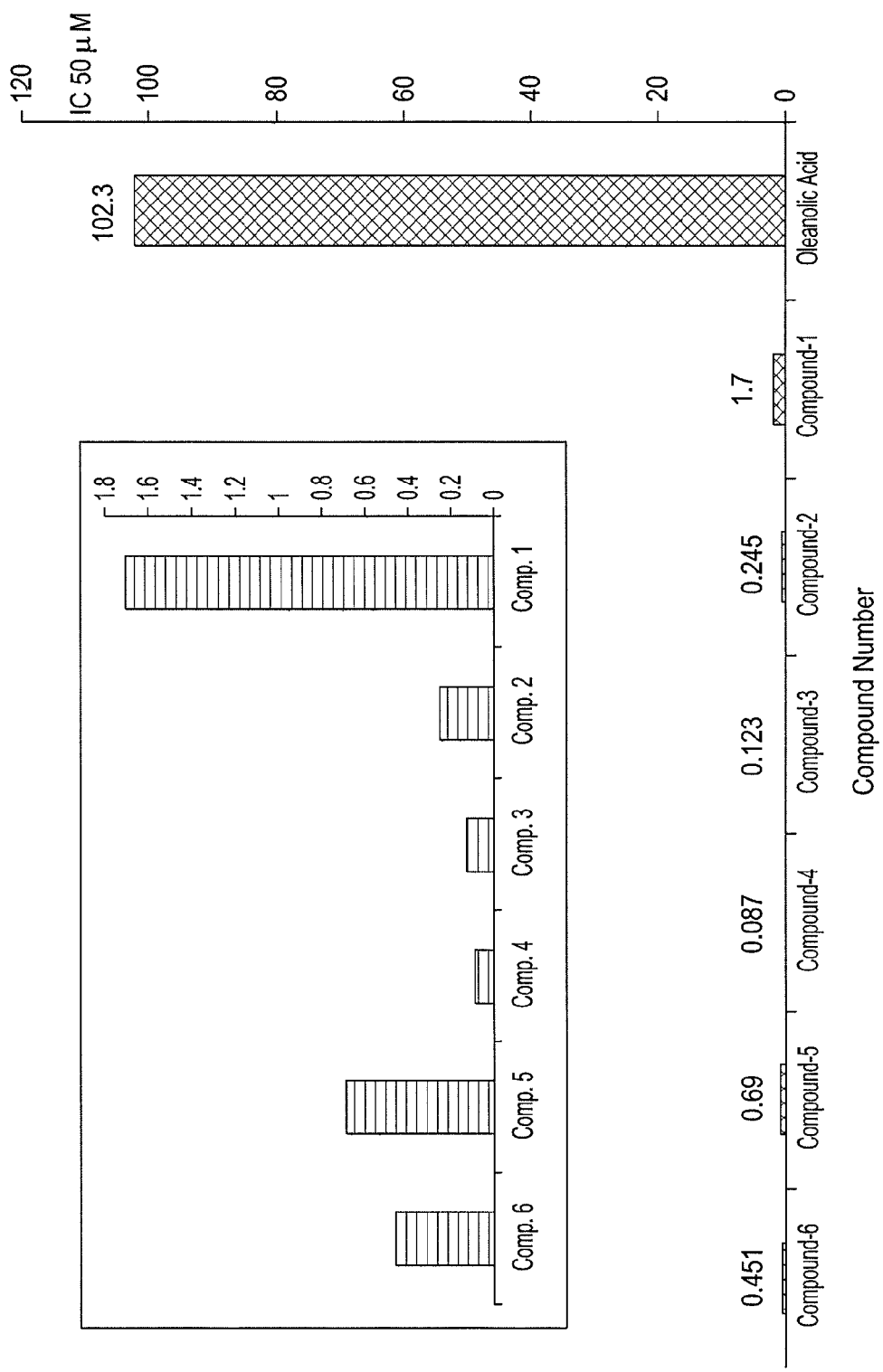
FIG. 4 is a graph showing relative α-Glucosidase inhibitor activity ($IC_{50}$ concentrations) for Compounds 1-6, compared to oleanolic acid.

These results, comparing Compounds 1-6 with oleanolic acid, are also reflected in FIG. 4.

Example 2

In Vivo Oral Hypoglycemic Activity

Compounds 1-6 were evaluated for hypoglycemic activity in vivo in alloxan induced diabetic mice model screenings, in comparison to control, vehicle, and the reference antidiabetic drugs pioglitazone, oleanolic acid, and acarbose. The percentage change in blood glucose levels in diabetic mice after oral administration of the test compounds, at a concentration of 200 μg/kg body weight, were determined at 2, 4, 6, and 24 hours.

The synthesized compounds were screened for hypoglycemic activity in vivo using the alloxan-induced diabetic mice model. For the acute study, animals were fasted overnight and the fasting blood serum glucose (SG) level was determined at 0 hours. Then the compounds were administered at a fixed dose of 200 μg/kg body weight orally (homogenized suspension in 0.5% carboxymethyl cellulose (CMC) with Tween 80). Animals in the vehicle group were given an equal amount of 0.5% CMC, while those in the control group were maintained as is. Blood samples were removed from all animals at 2, 4, 6 and 24 hours and percentage change in SG was calculated. See, Dunn, J. S., Letchie, N. G., "Experimental alloxan diabetes in the rat," *The Lancet* 242(6265): 384-387 (1943); and Mourao R. H., Silva T. G., et al., "Synthesis and Biological Activity of Novel Acridinylidene and Benzylidene thiazolidinediones," *Eur. J. Med. Chem.*, 40: 1129-1133 (2005).

Compound 4 shows consistently the best results among the tested compounds, while Compounds 2, 3, 5, and 6 still consistently perform better than Compound 1, which itself provides better results than the reference antidiabetic drugs. The maximum activity was observed after six hours, suggesting that the target compounds are very potent with longer duration of action than the reference drug pioglitazone. The results are set forth in Table 4.

TABLE 4

Effect of Compounds 1-6 on Serum Glucose Levels In Diabetic Mice % Change in SG Over Time

| Compound No | 2 h | 4 h | 6 h | 24 h |
|---|---|---|---|---|
| Control | 1.21 ± 0.32 | 2.11 ± 0.32 | 2.45 ± 0.22 | −0.21 ± 0.2 |
| Vehicle | 5.09 ± 0.32 | 9.87 ± 0.43 | 9.89 ± 0.32 | 1.51 ± 0.2 |
| Pioglitazone | −32.16 ± 1.21 | −22.45 ± 1.22 | −12.34 ± 0.51 | −13.28 ± 0.1 |
| Oleanolic acid | −40.79 ± 1.20 | −48.66 ± 1.31 | −52.17 ± 1.31 | −51.01 ± 1.11 |
| Acarbose | −29.23 ± 0.54 | −27.87 ± 0.54 | −20.17 ± 0.54 | −22.39 ± 0.78 |
| 1 | −69.40 ± 0.76 | −71.89 ± 0.79 | −79.32 ± 0.83 | −73.29 ± 0.78 |

TABLE 4-continued

Effect of Compounds 1-6 on Serum Glucose Levels In Diabetic Mice % Change in SG Over Time

| Compound No | 2 h | 4 h | 6 h | 24 h |
|---|---|---|---|---|
| 2 | −74.70 ± 0.67 | −81.67 ± 0.90 | −84.30 ± 0.47 | −80.78 ± 0.90 |
| 3 | −75.78 ± 0.65 | −82.76 ± 0.90 | −85.87 ± 0.87 | −79.67 ± 0.80 |
| 4 | −78.88 ± 0.79 | −85.89 ± 0.88 | −90.00 ± 0.78 | −88.88 ± 0.99 |
| 5 | −70.60 ± 0.89 | −79.01 ± 0.68 | −80.43 ± 0.89 | −75.41 ± 0.76 |
| 6 | −73.60 ± 0.47 | −80.74 ± 0.89 | −82.33 ± 0.58 | −77.80 ± 0.89 |

Values are mean ± S.E.M, n = 6 in each group. Statistical analysis by one way ANOVA followed by Dunnet test using Graphpad Instat software. ($P < 0.05$).

Figure 5:
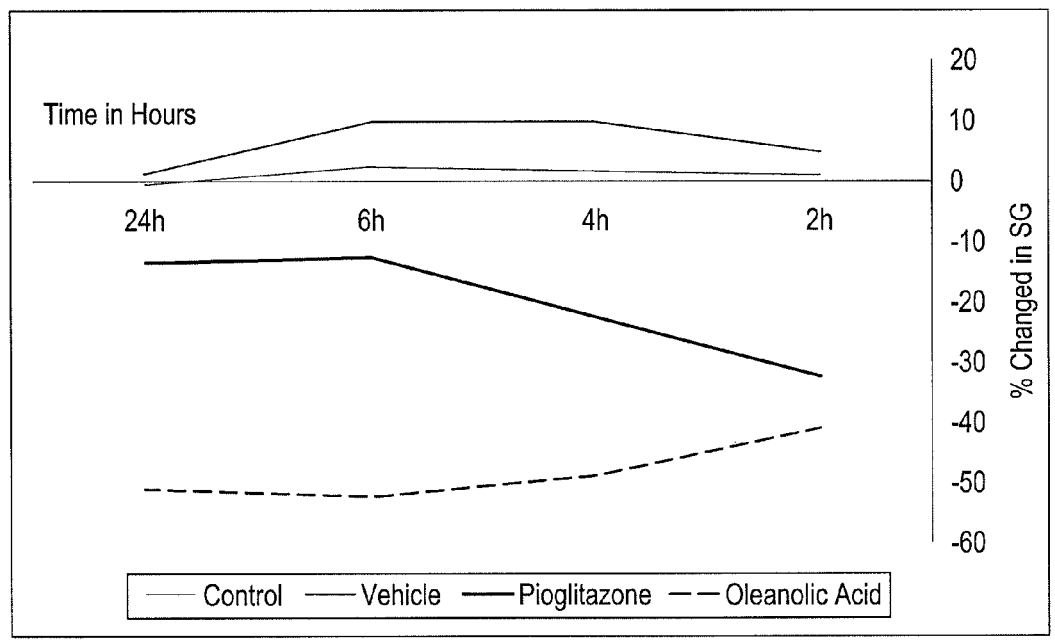
FIG. 5 is a graph plots showing the effect on serum glucose (SG) in diabetic mice, reflecting percent change in SG for dosing at 200 μg/kg body weight in an acute study (over a period of 24 hours) comparing control, vehicle, pioglitazone, and oleanolic acid.
Figure 6:
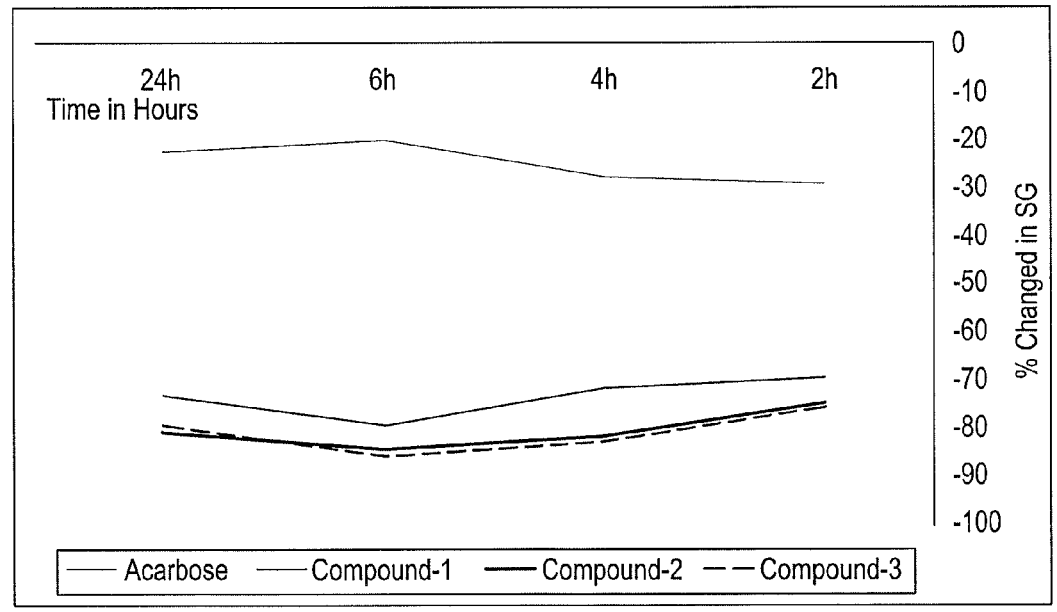
FIG. 6 is a graph showing the effect on serum glucose (SG) in diabetic mice, reflecting percent change in SG for dosing at 200 μg/kg body weight in an acute study (over a period of 24 hours) comparing acarbose and Compounds 1-3.
Figure 7:
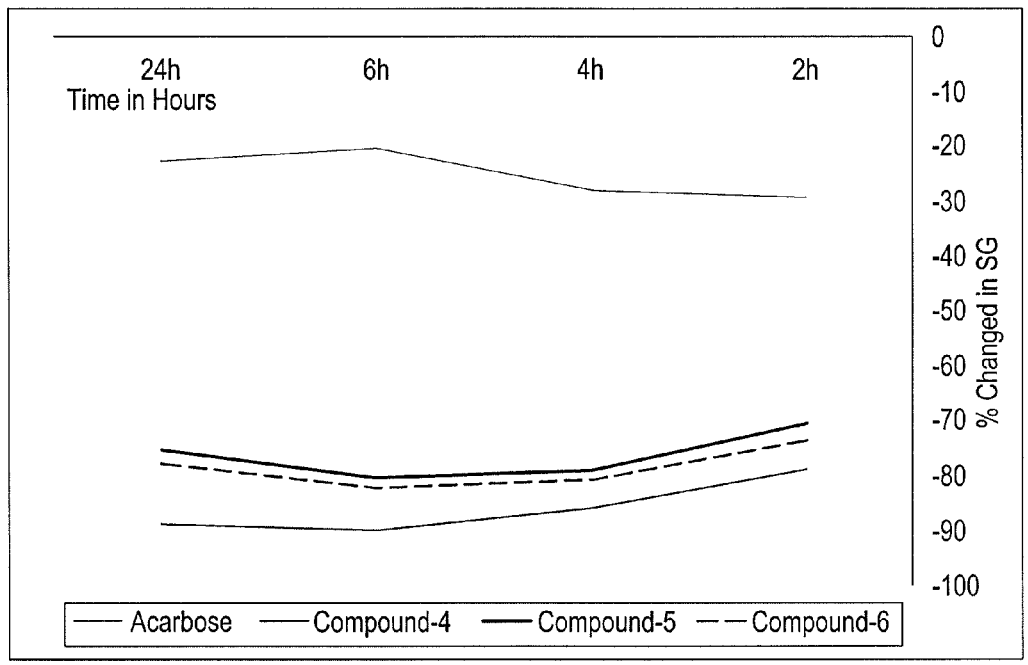
FIG. 7 is a graph showing the effect on serum glucose (SG) in diabetic mice, reflecting percent change in SG for dosing at 200 μg/kg body weight in an acute study (over a period of 24 hours) comparing acarbose and Compounds 4-6.

These results are also reflected in FIGS. 5 to 7—three graphs plotting the percent changes in serum glucose levels at 2 hours, 4 hours, 6 hours, and 24 hours post-administration. FIG. 5 provides the results for the control, vehicle, pioglitazone, and oleanolic acid. FIG. 6 provides the results for acarbose and Compounds 1-3. FIG. 7 provides results for acarbose and Compounds 4-6. All of Compounds 1-6 demonstrated much higher efficacy throughout the 24-hour period compared to pioglitazone, oleanolic acid, or acarbose.

These results are consistent with the DPP-IV inhibition activities discussed above and reported at Table 1. All of Compounds 1-6 showed higher activity than the reference antidiabetic drugs piolitazone, oleanolic acid and acarbose. Indeed, all of Compounds 1-6 exhibited more than double the activity of pioglitazone and acarbose, and almost double the activity of oleanolic acid, after 2 hours post-administration. The maximum activity for each of Compounds 1-6 was observed after 6 hours post-administration, suggesting that each of these compounds was both very potent, and had longer duration of action than, for example, the reference drug pioglitazone, which peaked at 2 hours post-administration, at less than half the activity of each of Compounds 1-6.

For the sub-acute study, Compounds 1-6 were then screened in vivo for their oral hypoglycemic activity after several days of their administration in alloxan induced diabetic mice model, i.e., through 21 days, followed by a 7-day rest period, post-administration in alloxan-induced diabetic mice. Study animals were fasted overnight, and the fasting SG levels calculated at 0 days. The test compounds were administered at a fixed dose of 200 µg/kg body weight orally (homogenized suspension in 0.5% CMC and permissible amounts of Tween 80) for 21 days at a fixed time. After 21 days, treatment was stopped and animals were left for a rest period of 7 days. Animals in the vehicle group were given an equal amount of 0.5% CMC, while those in the control group were maintained as is. During the study, blood samples were removed from all animals at 7, 14, 21 and 28 days, and the percentage change in SG was calculated. The data obtained were analyzed by one-way ANOVA followed by the Dunnett test. The results were expressed as mean±standard error of mean (SEM) for each group, while $p<0.01$ or $p<0.05$ was considered to be statistically significant. The percentage changes in blood glucose levels after oral administration, at 200 µg/kg body weight, were evaluated, and are reported in Table 5.

TABLE 5

Effect of Compounds 1-6 On Serum Glucose Levels in Diabetic Mice % Change in SG Over Time

| Compound No | 7 day | 14 day | 21 day | 7 days rest period |
|---|---|---|---|---|
| Control | 1.2 | 1.34 | 1.45 | 1.67 |
| Vehicle | 6.45 | 7.65 | 8.76 | 9.87 |
| Pioglitazone | −11.23 ± 0.12 | −18.34 ± 0.64 | −50.39 ± 0.20 | −43.45 ± 0.54 |
| Oleanolic acid | −10.56 ± 0.80 | −20.35 ± 0.72 | −37.68 ± 0.78 | −30.32 ± 0.83 |
| Acarbose | −18.29 ± 0.32 | −24.55 ± 0.63 | −31.78 ± 0.78 | −27.65 ± 0.74 |
| 1 | −59.76 ± 0.78 | −68.78 ± 0.65 | −84.65 ± 0.34 | −81.20 ± 0.58 |
| 2 | −62.35 ± 0.54 | −71.78 ± 0.78 | −87.54 ± 0.62 | −86.25 ± 0.66 |
| 3 | −66.76 ± 0.78 | −73.65 ± 0.77 | −89.76 ± 0.98 | −83.56 ± 0.46 |
| 4 | −67.90 ± 0.64 | −74.78 ± 0.09 | −90.87 ± 0.56 | −86.43 ± 0.87 |
| 5 | −60.89 ± 0.79 | −70.53 ± 0.89 | −85.45 ± 0.24 | −84.29 ± 0.687 |
| 6 | −61.68 ± 0.78 | −70.54 ± 0.89 | −86.45 ± 0.57 | −85.89 ± 0.579 |

Values are mean ± S.E.M, n = 6 in each group. Statistical analysis by one way ANOVA followed by Dunnet test using Graphpad Instat software. ($P < 0.05$).

Figure 8:
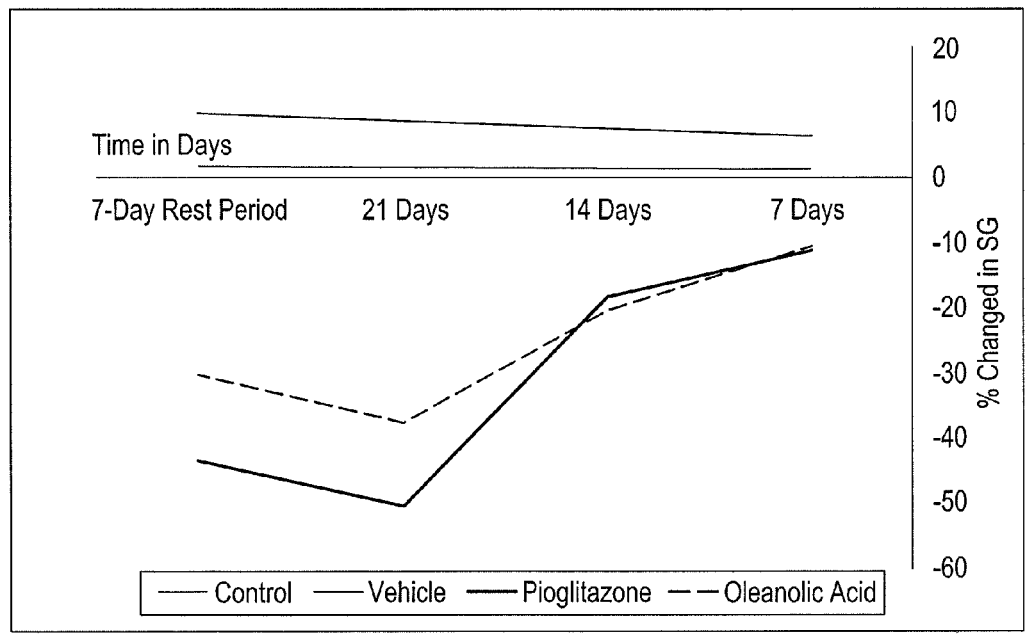
FIG. 8 is a graph showing effect of compounds on serum glucose (SG) in diabetic mice, reflecting percent change in SG for dosing at 200 μg/kg body weight, in a subacute study (over a period including 21 days of treatment followed by a 7-day rest period), comparing control, vehicle, pioglitazone, and oleanolic acid.
Figure 9:
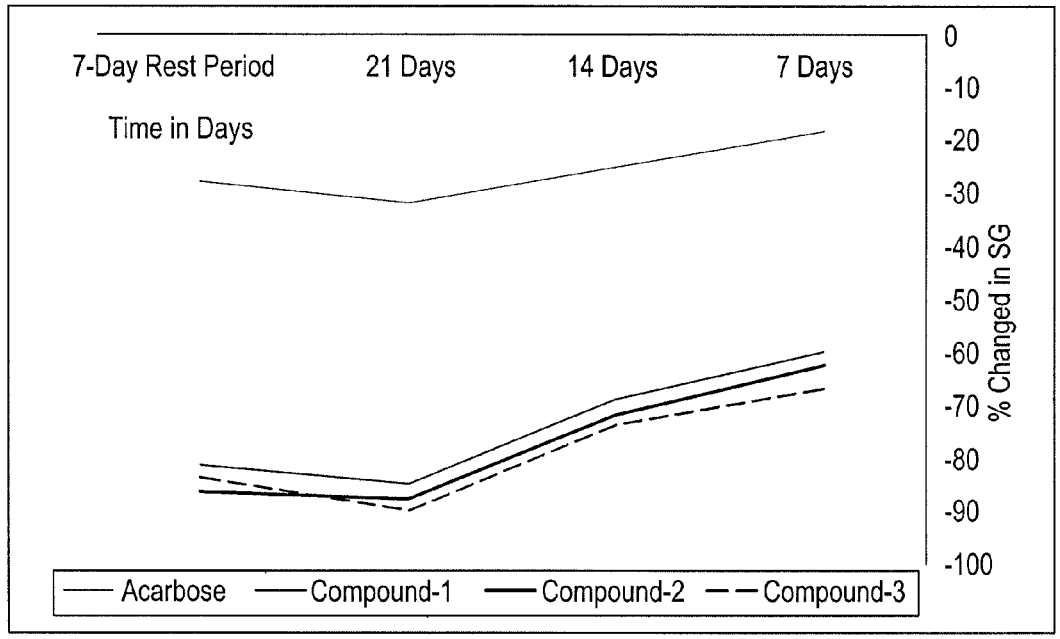
FIG. 9 is a graph showing effect of compounds on serum glucose (SG) in diabetic mice, reflecting percent change in SG for dosing at 200 μg/kg body weight, in a subacute study (over a period including 21 days of treatment followed by a 7-day rest period), comparing acarbose and compounds 1-3.
Figure 10:
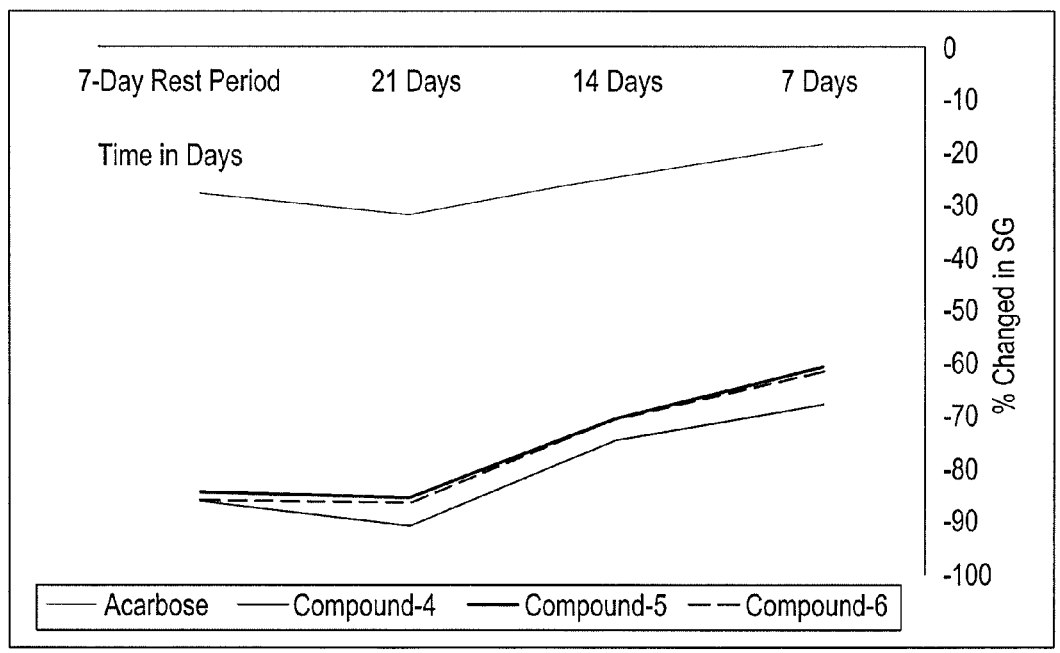
FIG. 10 is a graph showing effect of compounds on serum glucose (SG) in diabetic mice, reflecting percent change in SG for dosing at 200 μg/kg body weight, in a subacute study (over a period including 21 days of treatment followed by a 7-day rest period), comparing acarbose and compounds 4-6.

These results are also reflected in FIGS. 8 to 10—three graphs plotting the percent changes in serum glucose levels at 7 days, 14 days, 21 days, and after a 7-day rest period. FIG. 8 provides the results for control, vehicle, pioglitazone, and oleanolic acid. FIG. 9 provides results for acarbose, and Compounds 1-3. And FIG. 10 provides the results for acarbose and Compounds 4-6.

While the efficacy for all active compounds was greatest at the 21-day point, and then somewhat lower after the subsequent 7-day rest period, Compounds 1-6 presented consistently much greater effect than reference drugs pioglitazone, oleanolic acid, and acarbose at every time point measured. In particular, for example, the reference drugs pioglitazone, oleanolic acid, and acarbose averaged reductions of 13.36% after 7 days; 21.08% after 14 days; 39.95% after 21 days; and 33.81% after the 7-day rest period. In stark contrast, Compounds 1-6 averaged reductions of 63.22% after 7 days; 71.68% after 14 days; 87.45% after 21 days; and 84.60% after the 7-day rest period.

Thus, Compounds 1-6 averaged a 4.7× greater effect compared to the reference drugs after 7 days; a 3.4× greater effect after 14 days; a 2.19× greater effect after 21 days; and a 2.50× greater effect even after the 7-day rest period. And in each instance, each of Compounds 2-6 demonstrated at least some degree of increased efficacy compared to Compound 1.

It also was clear that the study animals still presented reduced blood glucose levels even after the 7-days rest period. These results again are consistent with the results reported above for both the DPP-IV inhibition activity (Table 1) and the acute in vivo study (Table 4).

It is evident that the most potent antidiabetic compounds, Compounds 2-4, all include the pyridine moiety. In comparing the relative efficacy to the structure of Compounds 2-6 as compared to each other and to Compound 1, it appears that the pyridine moiety provides the most potent antidiabetic activities. The morpholine moiety also increases antidiabetic activities, though not quite as much as the pyridine moiety. The phenyl moiety at position 4 of the olean skeleton further increases antidiabetic activities. Compound 1, without any of these moieties, provides increased efficacy compared to the prior art treating agents, while each of Compounds 2-6 provide even greater efficacy than Compound 1.

Example 3

Synthesis of Compounds 2-6

All melting points are uncorrected, and were measured using an electrothermal capillary melting point apparatus. The IR spectra were recorded on a Shimadzu FT-IR 8101 PC infrared spectrophotometer. The $^1$H-NMR spectra were determined with Bruker AM-200 MHz spectrometer. The chemical shifts are expressed on the δ (ppm) scale using TMS as the standard reference. Mass spectra were recorded on Finnigan SSQ operating at 70 ev. Elemental analysis determined on a Perkin Elmer 240 (microanalysis), Microanalysis Center, Cairo University, Cairo, Egypt.

Synthesis of Methyl-2-{4-pyridylidene}-3-oxo-18β-Olean-12-en-28-oate (Compound 2)

A solution of Compound 1 (9.08 mg, 20 mmol) was prepared, with 4-pyridinecarboxaldehyde (1.9 mL, 20 mmol) in ethanol (100 mL) and aqueous potassium hydroxide (9 mL, 30%), and stirred for 12 hours at room temperature. The precipitate was collected by filtration and washed several times with water and dried, then crystallized from ethanol. Yield 88%, mp. 367° C., $[α]_D^{25}$=+133 (c1, CHCl$_3$); IR (KBr): 3052 (CH—Ar), 2922 (CH-aliph), 1746 (C=O), 1650 (enone) cm$^{-1}$. $^1$H NMR (pyridine-d$_5$): δ ppm 0.84 (d, α-1H, CH, C-5), 0.90 (s, β-3H, CH$_3$, C-25), 0.95 (s, α-3H, CH$_3$, C-29), 1.00 (s, β-3H, CH$_3$, C-30), 1.04 (d, α-1H, CH, C-1), 1.08 (s, β-3H, CH$_3$, C-26), 1.15 (s, β-3H, CH$_3$, C-24), 1.20 (m, α-H, CH, C-15), 1.25 (s, α-3H, CH$_3$, C-23), 1.30 (m, β-1H, CH, C-21), 1.35 (s, α-3H, CH$_3$, C-27), 1.38 (m, β-1H, CH, C-19), 1.42 (m, β-1H, CH, C-7), 1.45 (m, β-1H, CH, C-6), 1.50 (m, α-1H, CH, C-21), 1.55 (d, β-1H, CH, C-1), 1.58 (t, α-1H, CH, C-9), 1.68 (m, α-1H, CH, C-7), 1.86 (m, α-1H, CH, C-19), 1.90 (m, α-1H, CH, C-22), 1.94 (m, α-1H, CH, C-6), 1.97 (m, 2H, CH$_2$, C-11), 1.99 (m, β-1H, CH, C-16), 2.05 (m, β-1H, CH, C-22), 2.11 (t, α-1H, CH, C-16), 2.16 (m, β-H, CH, C-15), 3.36 (dd, β-1H, CH, C-18), 3.49 (s, 3H, COOCH$_3$, C-28), 5.58 (s, 1H, CH, C-12), 7.27-8.60 (m, 4H, pyridine-H), 7.81 (s, 1H, enone). $^{13}$C NMR (pyridine-d$_5$): δ ppm 39.56, 130.55, 210.24, 39.57, 55.56, 18.60, 33.71, 39.85, 48.44, 37.56, 23.51, 122.56, 144.79, 42.80, 28.45, 23.67, 46.36, 42.77, 46.89, 31.65, 34.45, 33.67, 28.85, 16.47, 15.69, 17.76, 26.54, 173.45, 33.46, 23.60 (C1-C30), 52.68 (OCH$_3$ ester, C28), 146.75 (benzylidene), 149.60, 149.60, 124.20, 124.20, 147.12, (Pyridine-C). MS (EI): m/z 543 (100%) [M$^+$]. Anal. C$_{37}$H$_{51}$O$_3$ (543): Found C, 81.75; H, 9.35; Calcd C, 81.76; H, 9.39.

Synthesis of Methyl-2-{phenyl-(4-pyridyl)-methane}-3-oxo-18β-olean-12-en-28-oate (Compound 3)

First, 6 mmol of magnesium turnings were weighed and placed in a test tube. Next, 6 mmol of bromobenzene was placed in a second test tube, and then diluted with approximately 1 mL of anhydrous diethyl ether. A Pasteur pipette was used to transfer enough of the bromobenzene/ether mixture from one test tube to just cover the magnesium in the other test tube. The test tube was covered with a small piece of foil, and placed into the sonicator, which was then turned on. After 1-2 minutes, the reaction was checked for progress. If the liquid is brown, the reaction has begun. If not, the reaction is checked again after another 2 minutes. If the mixture still has not turned brown, it may be necessary to add a small crystal of iodine to start the reaction.

The tube of brown-colored Grignard reagent was removed from the sonicator and returned to the hood. About 1 mL of ether was added to the remaining bromobenzene/ether mixture in the other test tube. A few drops of this bromobenzene/ether mixture was added to the magnesium/bromobenzene/ether mixture. The bromobenzene/ether mixture was added at a rate that keeps the reaction proceeding, as evidenced by bubbling, a brown color, and production of heat. Generally, it takes about 10-15 minutes to add all of the bromobenzene mixture.

Once all of the bromobenzene/ether was added, the reaction was monitored for loss of solvent and for signs of continued reaction. If the volume drops below 2 mL, a little fresh diethyl ether is added to the test tube. Once the reaction stopped, as evidenced by stoppage in bubbling and the disappearance of almost all of the magnesium, the reaction tube was placed back into the sonicator again for 2 minutes. The Grignard reagent was then ready for use in the second part of the synthesis of Compound 3.

In the second part of the synthesis of Compound 3, Compound 2 was carefully weighed out (2.172 gm, 4 mmol) into a clean, dry 50 mL Erlenmeyer flask. A magnetic stir bar was added, and Compound 2 was dissolved in about 20 mL of anhydrous diethyl ether. The Erlenmeyer flask was clamped and placed in an ice-bath with a stirrer, and the solution was stirred slowly. A Pasteur pipette was used to slowly transfer the Grignard reagent to the cold solution, in a drop-wise fashion, being careful to leave any unreacted magnesium behind in the test tube.

Once addition of the Grignard reagent was complete, the flask was removed from the ice-bath, while stirring continued at room temperature for about 5-10 minutes. During this short period of stirring, 5 mL of 5% H$_2$SO$_4$ was chilled for the next step of the experiment. To quench the reaction, 5 mL of chilled 5% H$_2$SO$_4$ (aq.) was slowly added to the reaction flask, with continued stirring.

The flask was swirled until the mixture was nearly free of undissolved solids. The basic magnesium salts were converted into water-soluble salts, while the alcohol product dissolves in the ether layer. The mixture was transferred to a separatory funnel, leaving behind any insoluble solids. The flask was rinsed with a small amount of ether; the ether rinse was added to the separatory funnel.

If the mixture in the separatory funnel did not form two obvious layers, a little more ether was added—with the total volume being about 10 mL. The funnel was shaken, and the layers were allowed to separate. The lower aqueous layer was drained off. The ether layer was washed with 3 mL of 5% H$_2$SO$_4$. The lower aqueous layer was drained and the ether layer was washed with 3 mL of saturated aqueous sodium chloride. The ether solution was collected and dried over anhydrous sodium sulfate. The solution was decanted into a clean filter flask, preferably a sidearm flask, and the Na$_2$SO$_4$ was rinsed with about 1 mL of ether. The ether solution then contained Compound 3, along with any unreacted starting material and reaction byproducts, principally biphenyl.

Yield 56%, m.p. 215° C., $[α]_D^{25}$=+126 (c1, CHCl$_3$); IR (KBr): 3049 (CH—Ar), 2933 (CH-aliph), 1747 (C=O) cm$^{-1}$. $^1$H NMR (pyridine-d$_5$): δ ppm 0.82 (d, α-1H, CH, C-5), 0.87 (s, β-3H, CH$_3$, C-25), 0.93 (s, α-3H, CH$_3$, C-29), 0.98 (s, β-3H, CH$_3$, C-30), 1.03 (d, α-1H, CH, C-1), 1.07 (s, β-3H, CH$_3$, C-26), 1.13 (s, β-3H, CH$_3$, C-24), 1.17 (m, α-H, CH, C-15), 1.20 (s, α-3H, CH₃, C-23), 1.26 (m, β-1H, CH, C-21), 1.31 (s, α-3H, CH₃, C-27), 1.35 (m, β-1H, CH, C-19), 1.40 (m, β-1H, CH, C-7), 1.44 (m, β-1H, CH, C-6), 1.49 (in, α-1H, CH, C-21), 1.53 (d, β-1H, CH, C-1), 1.58 (t, α-1H, CH, C-9), 1.71 (in, α-1H, CH, C-7), 1.79 (m, α-1H, CH, C-2), 1.84 (m, α-1H, CH, C-19), 1.88 (m, α-1H, CH, C-22), 1.92 (m, α-1H, CH, C-6), 1.95 (m, 2H, CH₂, C-11), 1.98 (m, β-1H, CH, C-16), 2.01 (m, β-1H, CH, C-22), 2.05 (t, α-1H, CH, C-16), 2.12 (m, β-H, CH, C-15), 3.32 (dd, β-1H, CH, C-18), 2.32 (s, 1H, Ar—CH—Pyridine), 3.53 (s, 3H, COOCH₃, C-28), 5.64 (s, 1H, CH, C-12), 7.17-7.25 (m, 5H, Ar—H), 7.35-8.62 (m, 4H, pyridine-H). ¹³C NMR (pyridine-d₅): δ ppm 39.75, 47.89, 211.14, 39.80, 55.78, 18.80, 33.98, 39.90, 48.66, 37.76, 23.68, 122.89, 145.11, 43.10, 28.65, 23.78, 46.75, 42.98, 47.00, 31.80, 34.90, 34.84, 28.83, 16.24, 15.43, 17.87, 26.87, 174.11, 34.00, 23.50 (C1-C30), 53.23 (OCH₃ ester, C28), 58.12 (Ar—CH-Pyridine), 149.60, 149.60, 124.20, 124.20, 147.10 (Pyridine-C), 145.40, 128.50, 128.50, 130.20, 130.20, 126.90 (Ar—C). MS (EI): m/z 621 (90%) [M⁺]. Anal. C₄₃H₅₇O₃ (621): Found C, 83.00; H, 9.21; Calcd C, 83.09; H, 9.17.

Synthesis of methyl-2-{(4-pyridyl)-N-morpholinyl-methane}-3-oxo-18β-olean-12-en-28-oate (Compound 4)

A mixture of compound 2 (5.43 gm, 10 mmol) and morpholine (1 mL, 12 mmol) in dioxane (100 mL) was refluxed for 7 hours. The solution was evaporated under reduced pressure to dryness, and the solid was dried and recrystallized from benzene to give Compound 4.

Yield 88%, m.p. 305° C., $[\alpha]_D^{25}$=+141 (c1, CHCl₃); IR (KBr): 3048 (CH—Ar), 2929 (CH-aliph), 1746 (C=O) cm⁻¹. ¹H NMR (pyridine-d₅): δ ppm 0.83 (d, α-1H, CH, C-5), 0.89 (s, 13-3H, CH₃, C-25), 0.95 (s, α-3H, CH₃, C-29), 1.01 (s, β-3H, CH₃, C-30), 1.04 (d, α-1H, CH, C-1), 1.09 (s, 13-3H, CH₃, C-26), 1.15 (s, β-3H, CH₃, C-24), 1.19 (m, α-H, CH, C-15), 1.23 (s, α-3H, CH₃, C-23), 1.29 (m, 13-1H, CH, C-21), 1.35 (s, α-3H, CH₃, C-27), 1.39 (m, β-1H, CH, C-19), 1.42 (m, β-1H, CH, C-7), 1.46 (m, β-1H, CH, C-6), 1.51 (m, α-1H, CH, C-21), 1.54 (d, β-1H, CH, C-1), 1.57 (t, α-1H, CH, C-9), 1.69 (m, α-1H, CH, C-7), 1.81 (m, α-1H, CH, C-2), 1.85 (m, α-1H, CH, C-19), 1.90 (m, α-1H, CH, C-22), 1.93 (m, α-1H, CH, C-6), 1.96 (m, 2H, CH₂, C-11), 1.99 (m, β-1H, CH, C-16), 2.03 (m, β-1H, CH, C-22), 2.09 (t, α-1H, CH, C-16), 2.15 (m, β-1H, CH, C-15), 2.85 (m, 4H, 2CH₂, NCH₂), 3.35 (dd, β-1H, CH, C-18), 3.43 (s, 1H, NCH-Pyridine), 3.50 (s, 3H, COOCH₃, C-28), 3.67 (m, 4H, 2CH₂, OCH₂, 5.61 (s, 1H, CH, C-12), 7.31-8.62 (m, 4H, pyridine-H). ¹³C NMR (pyridine-d₅): δ ppm 39.65, 47.77, 211.04, 39.75, 55.66, 18.61, 33.72, 39.83, 48.47, 37.54, 23.57, 122.60, 144.90, 42.89, 28.48, 23.61, 46.32, 42.74, 46.90, 31.67, 34.67, 33.88, 28.88, 16.44, 15.39, 17.74, 26.78, 173.89, 34.04, 23.57 (C1-C30), 53.00 (OCH₃ ester, C28), 52.81 (NCH-Pyridine), 149.62, 149.62, 124.22, 124.22, 147.17, (Pyridine-C). 46.70, 46.70, 68.10, 68.10 (Morpholino-C). MS (EI): m/z 630 (88%) [M⁺]. Anal. C₄₁H₆₀NO₄ (630): Found C, 78.00; H, 9.60; N, 2.19; Calcd C, 78.09; H, 9.52; N, 2.22.

Synthesis of Methyl-2-{N-(morpholino)methane}-3-oxo-18β-olean-12-ene-28-oate (Compound 5)

A mixture of morpholine (1.72 mL, 20 mmol) and para-formaldehyde (0.6 gm) in absolute ethanol (100 mL) is refluxed for 1 hour to form the enamine Mannich adduct base. Compound 1 (9.08 mg, 20 mmol) is added, and the reflux is continued for another 1 hour. The reaction mixture is evaporated under reduced pressure to dryness. The solid is then recrystallized from methanol. Yield 88%, mp. 277° C., $[\alpha]_D^{25}$=+102 (c1, CHCl3); IR (KBr): 2929 (CH-aliph), 1733 (C=O) cm-1. 1H NMR (pyridine-d5): δ ppm 0.80 (d, α-1H, CH, C-5), 0.85 (s, β-3H, CH3, C-25), 0.92 (s, α-3H, CH3, C-29), 0.98 (s, β-3H, CH3, C-30), 1.01 (d, α-1H, CH, C-1), 1.06 (s, β-3H, CH3, C-26), 1.11 (s, β-3H, CH3, C-24), 1.16 (m, α-H, CH, C-15), 1.20 (s, α-3H, CH3, C-23), 1.26 (m, β-1H, CH, C-21), 1.33 (s, α-3H, CH3, C-27), 1.36 (m, β-1H, CH, C-19), 1.39 (m, β-1H, CH, C-7), 1.43 (m, β-1H, CH, C-6), 1.49 (m, α-1H, CH, C-21), 1.52 (d, β-1H, CH, C-1), 1.54 (t, α-1H, CH, C-9), 1.65 (m, α-1H, CH, C-7), 1.79 (m, α-1H, CH, C-2), 1.82 (m, α-1H, CH, C-19), 1.88 (m, α-1H, CH, C-22), 1.92 (m, α-1H, CH, C-6), 1.96 (m, 2H, CH2, C-11), 1.99 (m, β-1H, CH, C-16), 2.05 (m, β-1H, CH, C-22), 2.11 (t, α-1H, CH, C-16), 2.16 (m, β-H, CH, C-15), 2.83 (m, 4H, 2CH2, NCH2), 3.37 (dd, β-1H, CH, C-18), 2.51 (d, 1H, NCH2), 3.49 (s, 3H, COOCH3, C-28), 3.67 (m, 4H, 2CH2, OCH2), 5.67 (s, 1H, CH, C-12). 13C NMR (pyridine-d5): β ppm 39.89, 47.89, 211.00, 39.11, 55.56, 18.65, 33.75, 39.87, 48.48, 37.56, 23.55, 122.64, 144.93, 42.98, 28.55, 23.78, 46.79, 42.59, 46.90, 31.99, 34.96, 33.85, 28.48, 16.45, 15.46, 17.34, 26.78, 173.89, 34.04, 23.57 (C1-C30), 53.00 (OCH3 ester, C28), 38.71 (NCH); 46.70, 46.70, 68.10, 68.10 (Morpholino-C). MS (EI): m/z 567 (88%) [M+]. Anal. C36H57NO4 (567): Found C, 76.20; H, 10.05; N, 2.47; Calcd C, 76.19; H, 10.05; N, 2.46.

Synthesis of Methyl-2-{N-(morpholino) methane}-3β-hydroxy-3α-phenyl-18β-Olean-12-ene-28-oate (Compound 6)

Compound 1 is reacted as described above with regard to synthesis of Compound 4 from Compound 2. Phenyl magnesium bromide and the Grignard reagent are produced and reacted as described above regarding synthesis of Compound 3.

Yield 88%, mp. 277° C., $[\alpha]_D^{25}$=+102 (c1, CHCl₃); IR (KBr): 3530 (OH), 3041 (CH—Ar), 2933 (CH-aliph), 1729 (C=O) cm⁻¹. NMR (pyridine-d₅): β ppm 0.81 (d, α-1H, CH, C-5), 0.83 (s, β-3H, CH₃, C-25), 0.89 (s, α-3H, CH₃, C-29), 0.93 (s, β-3H, CH₃, C-30), 1.00 (d, α-1H, CH, C-1), 1.08 (s, β-3H, CH₃, C-26), 1.12 (s, 13-3H, CH₃, C-24), 1.17 (m, α-H, CH, C-15), 1.20 (s, α-3H, CH₃, C-23), 1.24 (m, β-1H, CH, C-21), 1.29 (s, α-3H, CH₃, C-27), 1.36 (m, β-1H, CH, C-19), 1.39 (m, β-1H, CH, C-7), 1.43 (m, β-1H, CH, C-6), 1.46 (m, α-1H, CH, C-21), 1.49 (d, β-1H, CH, C-1), 1.54 (t, α-1H, CH, C-9), 1.61 (m, α-1H, CH, C-7), 1.75 (m, α-1H, CH, C-2), 1.79 (m, α-1H, CH, C-19), 1.85 (m, α-1H, CH, C-22), 1.89 (m, α-1H, CH, C-6), 1.94 (m, 2H, CH₂, C-11), 1.96 (m, β-1H, CH, C-16), 2.07 (m, β-1H, CH, C-22), 2.10 (t, α-1H, CH, C-16), 2.14 (m, β-H, CH, C-15), 2.49 (d, 1H, NCH₂), 2.81 (m, 4H, 2CH₂, NCH₂), 3.33 (dd, β-1H, CH, C-18), 3.49 (s, 3H, COOCH₃, C-28), 3.67 (m, 4H, 2CH₂, OCH₂), 4.24 (s, 1H, OH), 5.67 (s, 1H, CH, C-12), 7.17-7.25 (m, 5H, Ar—H). ¹³C NMR (pyridine-d₅): δ ppm 39.56, 47.78, 65.99, 39.54, 55.79, 18.32, 33.69, 39.79, 48.69, 37.80, 23.84, 122.67, 144.89, 42.48, 28.86, 23.47, 46.56, 42.78, 46.90, 31.65, 34.36, 33.84, 28.48, 16.55, 15.46, 17.74, 26.88, 173.65, 34.44, 23.37 (C1-C30), 53.30 (OCH₃ ester, C28), 38.73 (NCH); 46.74, 46.75, 68.16, 68.25 (Morpholino-C), 45.42, 128.53, 128.53, 130.25, 130.25, 126.90 (Ar—C). MS (EI): m/z 645 (46%) [M⁺]. Anal. C₄₂H₆₃NO₄ (645): Found C, 78.15; H, 9.74; N, 2.15; Calcd C, 78.13; H, 9.76; N, 2.17.

It is to be understood that the oleanolic acid methyl ester derivatives having potent anti-diabetic activities are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An oleanolic acid methyl ester derivative selected from the group consisting of:

Compound 2, having the following structural formula

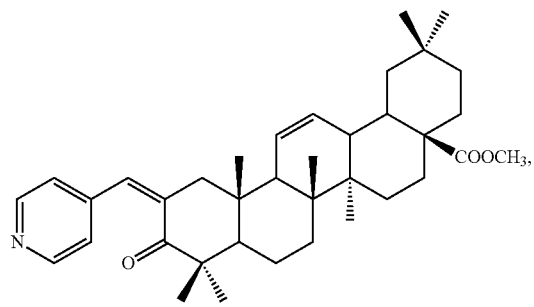

Compound 3, having the following structural formula

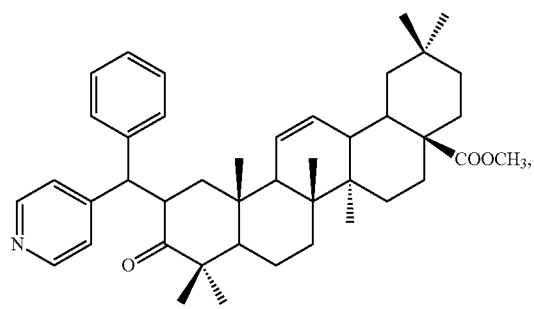

Compound 4, having the following structural formula

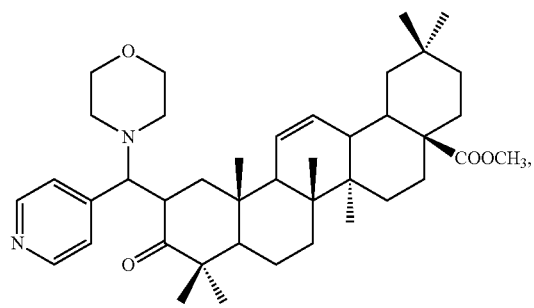

Compound 5, having the following structural formula

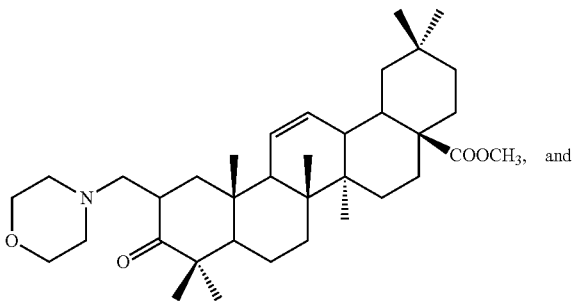

Compound 6, having the following structural formula

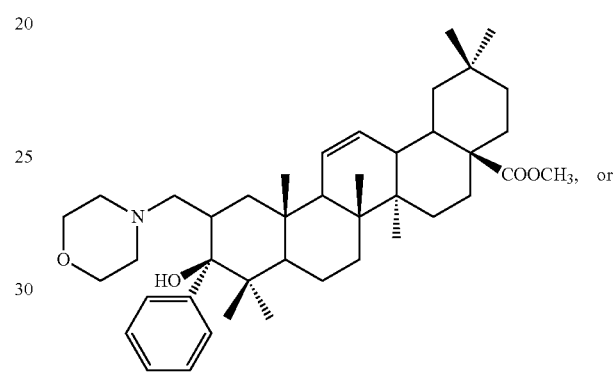

a pharmaceutically acceptable salt thereof.

2. The oleanolic acid methyl ester derivative of claim 1, wherein the compound is Compound 2.

3. The oleanolic acid methyl ester derivative of claim 1, wherein the compound is Compound 3.

4. The oleanolic acid methyl ester derivative of claim 1, wherein the compound is Compound 4.

5. The oleanolic acid methyl ester derivative of claim 1, wherein the compound is Compound 5.

6. The oleanolic acid methyl ester derivative of claim 1, wherein the compound is Compound 6.

7. A pharmaceutical composition, comprising the compound of claim 1 and a pharmaceutically acceptable carrier.

8. A method for treating diabetes or metabolic syndrome, comprising administering an effective amount of the pharmaceutical composition of claim 7 to a patient in need thereof.

9. A method for preparing an oleanolic acid methyl ester derivative, comprising mixing 3-oxo-oleanolic acid methyl ester with 4-pyridinecarboxaldehyde to provide the oleanolic acid methyl ester derivative, the oleanolic acid methyl ester derivative Compound 2, having the structural formula

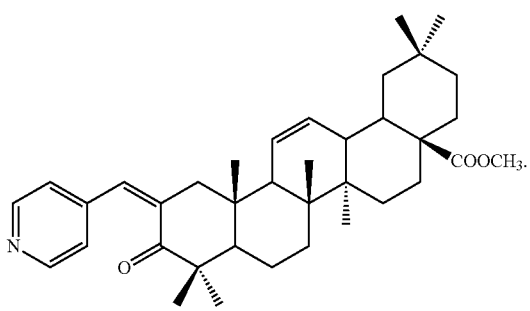

10. The method of claim 9, further comprising:
mixing Compound 2 with morpholine and dioxane to provide a mixture;
refluxing the mixture to provide a refluxed solution,
evaporating a dioxane in the refluxed solution under reduced pressure to provide the oleanolic acid methyl ester derivative, the oleanolic acid methyl ester derivative Compound 4, having the structural formula

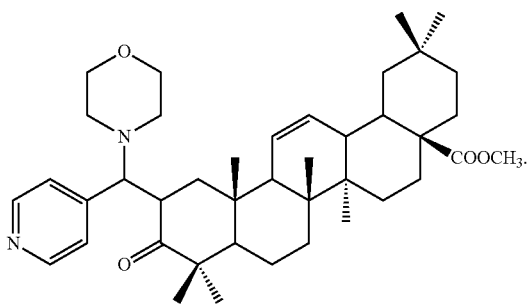

11. The method of claim 10, further comprising:
preparing phenylmagnesium bromide;
preparing a mixture of Compound 2 and Compound 4;
adding the phenylmagnesium bromide to the mixture under Grignard reaction conditions to provide the oleanolic acid methyl ester derivative, the oleanolic acid methyl ester derivative Compound 3, having the structural formula

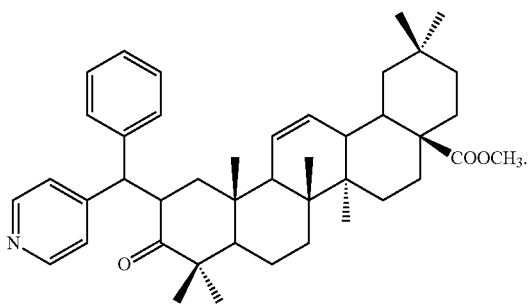

12. A method for preparing an oleanolic acid methyl ester derivative, comprising
mixing 3-oxo-oleanolic acid methyl ester with morpholine and paraformaldehyde under Mannich reaction conditions to provide the oleanolic acid methyl ester derivative, the oleanolic acid methyl ester derivative Compound 5, having the structural formula

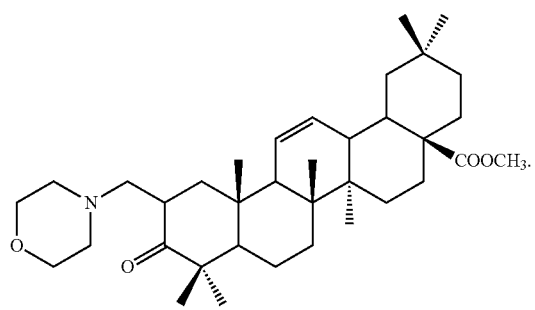

13. The method of claim 12, further comprising;
treating Compound 5 with phenyl magnesium bromide under Grignard reaction conditions to provide the oleanolic acid methyl ester derivative, the oleanolic acid methyl ester derivative Compound 6, having the structural formula

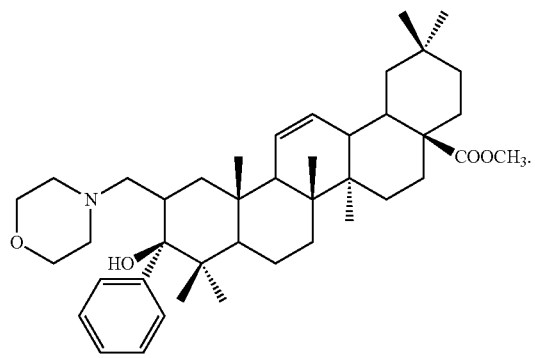

* * * * *